(12) United States Patent
Ennifar et al.

(10) Patent No.: US 7,547,712 B2
(45) Date of Patent: Jun. 16, 2009

(54) METHODS FOR DECREASING THE TOXIC EFFECTS OF NICOTINE ON FETUSES IN PREGNANT WOMEN

(75) Inventors: Sofiane Ennifar, Silver Spring, MD (US); Scott Winston, Boulder, CO (US); James Terrill, Gaithersburg, MD (US); Steve Fuller, Silver Spring, MD (US)

(73) Assignees: Nabi Biopharmaceuticals, Rockville, MD (US); United States of America as Represented by the Secretary, DHHS Office of Technology Transfer, National Institutes of Health, Rockville, MD (US)

( * ) Notice: Subject to any disclaimer, the term of this patent is extended or adjusted under 35 U.S.C. 154(b) by 0 days.

(21) Appl. No.: 11/679,022

(22) Filed: Feb. 26, 2007

(65) Prior Publication Data

US 2007/0212364 A1    Sep. 13, 2007

Related U.S. Application Data

(60) Provisional application No. 60/776,667, filed on Feb. 27, 2006.

(51) Int. Cl.
*A61K 31/465* (2006.01)
*C07D 401/00* (2006.01)

(52) U.S. Cl. .................................. 514/343; 546/279.4
(58) Field of Classification Search ....................... None
See application file for complete search history.

(56) References Cited

U.S. PATENT DOCUMENTS 6,232,082 B1 * 5/2001 Ennifar et al. ................. 435/7.1

FOREIGN PATENT DOCUMENTS

EP    1 512 414 A    3/2005

OTHER PUBLICATIONS

Keyler et al., Journal of Pharmacology and Experimental Therapeutics, 2003, 305: 587-592.*

Keyler et al., "Maternal vaccination against nicotine reduces nicotine distribution to fetal brain in rats," *Journal of Pharmacology and Experimental Therapeutics*, May 2003, pp. 587-592; vol. 305, No. 2.
Keyler et al., "Reduced nicotine distribution from mother to fetal brain in rats vaccinated against nicotine: Time course and influence of nicotine dosing regimen," *Biochemical Pharmacology*, May 2005, pp. 1385-1395, vol. 69, No. 9.
Nekhayeva et al., "Effects of nicotine-specific antibodies, Nic311 and Nic-igG, on the transfer of nicotine across the human placenta," *Biochemical Pharmacology*, Nov. 25, 2005, pp. 1664-1672, vol. 70, No. 11, Pergamon, Oxford GB.
Haustein, "Cigarette smoking, nicotine and pregnancy," *International Journal of Clinical Pharmacology and Therapeutics*, Sep. 1999, pp. 417-427, vol. 37, No. 9.
Chen et al., "Effect of prenatal or perinatal nicotine exposure on neonatal thyroid status and offspring growth in rats," *Life Sciences*, Jan. 28, 2005, pp. 1249-1258, vol. 76, No. 11, Pergamon Press, Oxford GB.
Malin et al, "Passive immunization against nicotine prevents nicotine alleviation of nicotine abstinence syndrome," *Pharmacology Biochemistry and Behavior*, Jan. 2001, pp. 87-92, vol. 68, No. 1.
Lessage, et al., "Current status of immunologic approaches to treating tobacco dependence: vaccines and nicotine-specific antibodies," *The AAPS Journal 2006*, Feb. 24, 2006, pp. E65-E75, vol. 8, No. 1.
Foulds et al., "Developments in pharmacotherapy for tobacco dependence: past, present and future," *Drug and Alcohol Review* Jan. 2006, pp. 59-71, vol. 25, No. 1.
Hatsukami et al., "Safety and immunogenicity of a nicotine conjugate vaccine in current smokers," *Clinical Pharmacology & Therapeutics*, Nov. 2005, pp. 456-467, vol. 78, No. 5, Mosby-Year Book, St. Louis, MO, US.
Keyler et al., "Changes in maternal and fetal nicotine distribution after maternal administration of monoclonal nicotine-specific antibody to rats," *International Immunopharmacology*, Nov. 2006, pp. 1665-1672, vol. 6, No. 11, Elsevier, Amsterdam, NL.
Heading, "NicVAX (Nabi Biopharmaceuticals)," *Idrugs: The Investigational Drugs Journal* Dec. 2003, pp. 1178-1181, vol. 6, No. 12.
Haney et al., "Therapeutic Vaccines for Substance Dependence," *Expert Review of Vaccines*, 2004, pp. 11-18, vol. 3, Future Drugs, London GB.

* cited by examiner

*Primary Examiner*—Ilia Ouspenski
(74) *Attorney, Agent, or Firm*—Foley & Lardner LLP

(57) ABSTRACT

The present invention relates methods for reducing the adverse effects of nicotine. This application describes the use of nicotine carrier conjugates in decreasing the toxic effects of nicotine on a fetus.

20 Claims, No Drawings

METHODS FOR DECREASING THE TOXIC EFFECTS OF NICOTINE ON FETUSES IN PREGNANT WOMEN

BACKGROUND

1. Field of the Invention

The present invention relates methods for reducing the adverse effects of nicotine. In particular, this application describes the use of nicotine carrier conjugates in decreasing the toxic effects of nicotine on a fetus.

2. Background of the Invention

Nicotine use is widespread due to the easy availability of cigarettes, cigars, pipes and smokeless tobacco. Nicotine is an alkaloid derived from the tobacco plant that is responsible for smoking's psychoactive and addictive effects. According to the American Society for Reproductive Medicine, cigarette smoking has an adverse impact on fertility and is associated with a greater incidence of spontaneous miscarriage and possibly ectopic pregnancy. Also, the U.S. Department of Health and Human Services indicates that cigarette smoking during pregnancy increases one's chances of problems during pregnancy, including premature or early birth, and having a baby with low birth weight. Similarly, exposure to second-hand smoke during pregnancy also has been reported to have detrimental health effects.

Thus, there is a need in the art for compositions and methods for ameliorating the adverse effects of smoking and/or second-hand smoke during pregnancy, and of nicotine in particular, on a fetus. The present application satisfies these needs.

SUMMARY OF THE INVENTION

The present invention describes a method for reducing at least one adverse effect of nicotine on a fetus, such as low birth weight, premature delivery/birth, post-natal nicotine withdrawal and fetal death, comprising administering a nicotine-carrier conjugate to a mammal of child-bearing age. In one embodiment, the mammal of child-bearing age is a human pregnant with a fetus. In another embodiment, the fetus is exposed to nicotine via nicotine-containing smoke inhaled by the human pregnant with the fetus, a smokeless tobacco product or nicotine replacement therapy. The smoke may be inhaled by the human pregnant with the fetus from a cigarette, pipe or cigar.

Similarly, the present invention contemplates reducing at least one adverse effect of nicotine on a fetus wherein the fetus is exposed to nicotine by a smokeless tobacco product such as a nicotine transdermal patch, chewing tobacco, snuff, tobacco pouches, nicotine-containing chewing gum, inhaler, nasal spray, tobacco lozenges, and sucker, or from second-hand smoke. The fetus may also be exposed to nicotine when the mammal of child-bearing age smokes at least about 1 cigarette per day, and/or has a plasma nicotine level of a chronic smoker and/or of an occasional smoker, and/or has a plasma nicotine level that is detectable. For example, the mammal of child-bearing age may have a plasma nicotine level of at least about 10 ng/mL.

The method of the present invention contemplates administering a nicotine-carrier conjugate, wherein the nicotine-carrier conjugate is administered in a dose of about 0.35 µg/kg to about 6 µg/kg, and preferably, at a dose of 2.5 µg/kg. In one embodiment, one dose of nicotine carrier conjugate is administered to the mammal of child-bearing age. In another embodiment, multiple doses of nicotine carrier conjugate are administered to the mammal of child-bearing age. The conjugate can be administered to the mammal before she becomes pregnant and/or after she becomes pregnant.

Also described in the present invention are methods for increasing the gestation time of a fetus to the maximum normal gestational period in a pregnant mammal exposed to nicotine, comprising administering a nicotine-carrier conjugate to the pregnant mammal; methods for reducing the risk of spontaneous abortion of a fetus from a pregnant mammal exposed to nicotine, relative to the risk of abortion in a pregnant mammal not exposed to nicotine, comprising administering a nicotine-carrier conjugate to the pregnant mammal; methods for increasing the fertility of a female mammal exposed to nicotine, comprising administering a nicotine-carrier conjugate to the female mammal, wherein the female mammal is attempting to get pregnant; and methods for reducing at least one adverse effect of nicotine on a fetus, comprising administering an antibody which binds a nicotine-carrier conjugate to an mammal of child-bearing age.

Methods for inducing a protective response against nicotine in a mammal pregnant with a fetus, comprising administering a nicotine-carrier conjugate to the pregnant mammal at least one time during pregnancy are also disclosed herein. In one embodiment, the nicotine-carrier conjugate is administered in a dose of about 0.35 µg/kg to about 6 µg/kg.

DETAILED DESCRIPTION OF THE INVENTION

The present inventors have surprisingly discovered that use of a nicotine vaccine can ameliorate the adverse effects of nicotine on a fetus in a pregnant animal. In particular, the inventors discovered that a nicotine vaccine can enhance fetal survival in an animal exposed to nicotine during pregnancy.

As described herein, a nicotine vaccine comprises a nicotine carrier conjugate that comprises a nicotine hapten conjugated to an immunogenic carrier protein. The term "hapten," as used in the present invention refers to a low-molecular weight organic compound that is not capable of eliciting an immune response by itself but will elicit an immune response once attached to a carrier molecule. A hapten of the present invention is a nicotine derivative and this nicotine hapten contains a reactive functional group, to which the carrier can be attached directly, or via a linker, or via a matrix, or via a linker and a matrix. Preferably, the nicotine hapten is attached to the carrier protein via an amide or disulfide bond. Amide and disulfide bonds have the desirable property of stability and because the hapten-carrier conjugates of the invention will be used as vaccines, it is important that the conjugates are stable, to prolong the shelf life of the vaccine.

In one embodiment of the present invention, the nicotine hapten is represented by the formula:

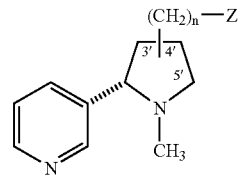

wherein n is 0 to 12 and Z is $NH_2$, COOH, CHO or SH and $-(CH_2)_n-Z$ can be bonded to the 3', 4' or 5' position. The Z moiety is capable of binding to a carrier, directly or via a linker. The carrier-hapten conjugate will induce the production of antibodies upon its introduction into the body of a patient or an animal.

In another embodiment, the nicotine hapten is of the following formula (3'-aminomethyl nicotine):

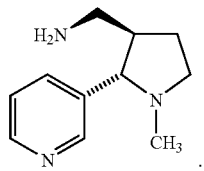

As stated above, the nicotine haptens described herein are conjugated to a carrier protein. The carrier proteins for use in the nicotine carrier conjugate can be any immunogenic protein or polypeptide. For example, in one embodiment, the carrier protein will comprise a T-cell epitope, a multi-antigenic peptide, bacterial toxins such as diphtheria, cholera, and tetanus and their corresponding toxoids, α toxin, and exotoxin protein A. A suitable nicotine carrier conjugate is described in U.S. Pat. No. 6,232,082 and is incorporated by reference in its entirety.

The nicotine carrier conjugate may be made as a direct conjugate, i.e., a single nicotine hapten is directly attached to a carrier with or without a linker, or as a matrix conjugate, where a number of haptens can be attached to a carrier by using a matrix. Suitable matrices include an amino acid, a peptide, dipeptide or a polypeptide. Methods for making direct and matrix conjugates are known in the art. See, for example, G. T. Hermanson, BIOCONJUGATE TECHNIQUES, Academic Press (1996); Dick and Beurret, *Contribu. Microbiol. Immnol.*, 10:48-114 (1989); Green, PROTECTIVE GROUPS IN ORGANIC CHEMISTRY, John Wiley & Sons, New York (1991); and Wong, CHEMISTRY OF PROTEIN CONJUGATION AND CROSS-LINKING, CRC Press, Inc. (1991). Thus, the nicotine carrier conjugate is prepared by reacting one or more haptens with a carrier protein by techniques known in the art. The resulting hapten carrier conjugate is capable of stimulating T cells, which leads to T cell proliferation and release of mediators which activate specific B cells to stimulate antibody production in response to the immunogenic hapten carrier conjugate.

The nicotine carrier conjugate described herein can also be formulated as a vaccine for active immunization. The vaccine composition of the present invention comprises at least one nicotine hapten carrier conjugate in an amount sufficient to elicit an immune response thereto. The nicotine hapten carrier conjugate is capable of remaining in vivo at a concentration sufficient to be active against subsequent nicotine intake.

Initial vaccination with the nicotine hapten carrier conjugate of the present invention creates high titers of antibodies that are specific to nicotine. The therapeutically effective amount of a conjugate which is administered to a patient in need is readily determined by a skilled artisan. Suitable dosage ranges are about 0.35 μg/kg to about 50 μg/kg, and it generally takes a patient one to several weeks to generate antibodies against a foreign antigen. In one embodiment, a suitable dosage range is about 0.35 μg/kg to about 6 μg/kg. In another embodiment, suitable dosage ranges are about 25 μg per dose to about 500 μg per dose with one to five doses, and about 25 μg per dose to about 400 μg per dose, with one to five doses. The term "about 1 μg/kg" refers to +/−5 μg/kg. A preferred dosage range is 2.5 μg/kg, which may be administered one time (single dose) or in multiple doses. The vaccine may also be administered before pregnancy and/or during pregnancy. In one embodiment, the vaccine is administered as early in pregnancy as possible, for example before 12 weeks, before 10 weeks, before 8 weeks, before 6 weeks, before 5 weeks, before 4 weeks, before 3 weeks, before 2 weeks, or before 1 week of pregnancy. In another embodiment, the vaccine is administered during pregnancy, either as a single dose or as a multi-dosing scheme. For example, the vaccine may be administered in the first trimester of pregnancy, such as when the mammal of child-bearing age is at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, or at least 12 weeks of pregnancy. Similarly, the present invention also contemplates administering the vaccine before pregnancy and also during pregnancy. The production of antibodies in a patient's blood can be monitored by using techniques that are well known to the skilled artisan, such as by ELISA, radioimmunoassay, and Western blotting methods.

The nicotine vaccines described herein may contain at least one adjuvant. The adjuvant used in the present invention is selected so as to not inhibit the effect of the carrier protein. Adjuvants suitable for use in the present invention include those that are physiologically acceptable to humans, including alum, QS-21, saponin and monophosphoryl lipid A.

Furthermore, the nicotine vaccines described herein may optionally contain one or more pharmaceutically acceptable excipients. The excipients useful in the present invention include, but are not limited to sterile water, salt solutions such as saline, sodium phosphate, sodium chloride, alcohol, gum arabic, vegetable oils, benzyl alcohols, polyethylene glycol, gelatin, mannitol, carbohydrates, magnesium stearate, viscous paraffin, fatty acid esters, hydroxyl methyl cellulose and buffers. Other excipients suitable for use in the present invention are known in the art. In addition to the usual pharmaceutically acceptable excipients, the composition may contain optional components to ensure purity, enhance the bioavailability and/or increase penetration.

Additionally, the vaccine formulation of the nicotine hapten carrier conjugate may optionally contain at least one auxiliary agent, including, but not limited to dispersion media, coatings, microsphere, liposomes, microcapsules, lipids, surfactants, lubricants, preservatives and stabilizers. Other auxiliary agents suitable for use in the vaccine formulation are known in the art.

Similarly, the pharmaceutical composition of the nicotine hapten carrier conjugate may contain additional components in order to protect the composition from infestation with, and growth of, microorganisms. In one embodiment, the composition is manufactured in the form of a lyophilized powder which is to be reconstituted by a pharmaceutically acceptable diluent just prior to administration. Methods of preparing sterile injectable solutions are well known to the skilled artisan and include but are not limited to drying, freeze-drying, and spin drying. These techniques yield a powder of the active ingredient with any additional excipient incorporated therein.

The vaccine formulation of the nicotine hapten carrier conjugate can be administered by a variety of means, including via intranasal, intrathecal, oral, dermal, subcutaneous, or intravenous modes of administration. When the composition containing the hapten carrier conjugate is to be sued for injection, it is preferable to solubilize the hapten carrier conjugate in an aqueous saline solution at a pharmaceutically acceptable pH. However, it is possible to use an injectable suspension of the hapten carrier conjugate.

Furthermore, the compositions described herein can be administered in multiple doses. For example, following initial administration of the nicotine vaccine, a subsequent administration of one or more "boosters" may follow. Such a booster will increase antibody production against the nicotine hapten carrier conjugate. However, a single dose of the nicotine carrier conjugate during pregnancy is also specifically contemplated.

Alternatively, anti-nicotine antibodies generated outside the body of the patient to be treated, in a suitable host mammal, can be administered to the patient. Thus, the nicotine carrier conjugate may be used to produce antibodies which are suitable for passive immunization. Passive immunization comprises administration of or exposure to a polyclonal antibody or monoclonal antibody which has been raised in response to a nicotine hapten carrier conjugate of the invention. Such antibodies can be generated in animals or humans. Antibodies raised in response to a nicotine conjugate of the invention can be administered to prevent the adverse effects of nicotine on a fetus. Antibodies raised by administration of the inventive hapten-carrier conjugate have a molecular weight range of from about 150 kDa to about 1,000 kDa.

In one embodiment, the present invention describes methods for reducing at least one adverse effect of nicotine on a fetus, comprising administering a nicotine carrier conjugate to an animal of child-bearing age. An adverse effect of nicotine includes, but is not limited to low birthweight, very low birthweight, premature delivery/birth (i.e., before the end of the $37^{th}$ week of pregnancy), post-natal nicotine withdrawal and fetal death. Low birthweight, as described herein, means less than 5 pounds, 8 ounces, and very low birthweight connotes less than 3 pounds, five ounces. Post-natal nicotine withdrawal is often characterized by symptoms of irratability, restlessness, difficulty sleeping, shaking, and tremors. Nicotine toxicity is also evidenced by lower maternal body weight, reduced food consumption and lower fetal survival. As described herein, the mammal of child-bearing age is an animal, such as a human, pregnant with a fetus. Alternatively, the mammal of child-bearing age is an animal that is not yet pregnant but has the ability to get pregnant and optionally, intends to get pregnant. Thus, it is also contemplated that the nicotine carrier conjugate is administered to the animal before she becomes pregnant.

In one aspect of the present invention, the fetus has been or is at risk to nicotine exposure via nicotine-containing smoke inhaled by the animal pregnant with the fetus. The smoke can be inhaled directly (eg., via smoking) by the animal pregnant with the fetus, or indirectly, by inhaling second-hand smoke generated by a cigarette, pipe or cigar. The mammal of child-bearing age may be a "chronic" smoker, i.e., smoke on average at least about 5, at least about 10, or at least about 15 cigarettes per day. In another embodiment, the mammal of child-bearing age may be an "occasional" smoker, eg., smoke on average at least about 1 cigarette per week, at least about 2 cigarettes per week, at least about 3 cigarettes per week, at least about 4 cigarettes per week, at least about 5 cigarettes per week, at least about 6 cigarettes per week, at least about one cigarette per day. The term "at least about" with regard to number of cigarettes means +/−2 cigarettes. Thus, "at least about five cigarettes" connotes anywhere from 3 to 7 cigarettes and "at least about 10 cigarettes" refers to anywhere from 8 to 12 cigarettes, etc.

In addition, or in the alternative, the mammal of child-bearing age may have a plasma nicotine level of a chronic or occasional smoker. For example, the mammal of child-bearing age may have a plasma nicotine level of about 5 to about 80 ng/ml, of about 10 to about 70 ng/ml, of about 15 to about 60 ng/ml, of about 20 to about 60 ng/ml, of about 25 to about 60 ng/ml, of about 30 to about 60 ng/ml or of about 40 to about 60 ng/ml. The term "of about" connotes +/−5 ng/ml plasma nicotine. Thus, "of about 10 to about 70 ng/ml" refers to a range of 5 ng/ml to 75 ng/ml. In another embodiment, the mammal of child-bearing age may have a plasma nicotine level of at least 1 ng/ml, at least 2 ng/ml, at least 3 ng/ml, at least 4 ng/ml, at least 5 ng/ml, at least about 10 ng/ml, at least about 15 ng/ml, at least about 20 ng/ml, at least about 25 ng/ml, at least about 30 ng/ml, at least about 40 ng/ml, at least about 50 ng/ml, at least about 60 ng/ml, at least about 70 ng/ml, or at least about 80 ng/ml. With regard to plasma nicotine levels, the term "at least about" connotes +/−5 ng/ml. Thus, "at least about 10 ng/ml" refers to a range of 5 ng/ml to 15 ngml.

Plasma nicotine levels can be measured by techniques known in the art, such as by high performance liquid chromatography (HPLC).

The fetus can also be exposed to nicotine from a smokeless tobacco product or nicotine replacement therapy. For example, the nicotine may come from a nicotine transdermal patch, chewing tobacco, snuff, tobacco pouch, nicotine-containing chewing gum, inhaler, nasal spray, tobacco lozenges, and sucker. In this regard, the mammal of child-bearing age may have a plasma nicotine level high enough to benefit from administration of a nicotine hapten carrier conjugate. A plasma level high enough to benefit from administration of a nicotine hapten carrier conjugate is at least 1 ng/ml.

The present invention also describes a method for increasing the gestation time of a fetus to the maximum normal gestational period in a pregnant animal exposed to nicotine, a method for reducing the risk of spontaneous abortion of a fetus from a pregnant animal exposed to nicotine, (relative to the risk of abortion in a pregnant animal not exposed to nicotine), and a method for inducing a protective response in an animal pregnant with a fetus against nicotine, comprising administering a nicotine-carrier conjugate at least one time to the animal during pregnancy. Another embodiment of the present invention is a method for increasing the fertility of a female animal exposed to nicotine, comprising administering a nicotine-carrier conjugate to the female animal, wherein the female animal is attempting to get pregnant.

The examples below are illustrative of embodiments of the current invention and should not be used, in any way, to limit the scope of the claims.

\* \* \*

EXAMPLES

Example 1

Seven groups of female, 6-8 month old, New Zealand White rabbits (195 total animals) were administered test or control articles three times by intramuscular injection on Days −30 and −9 Pre-Gestation and on Gestation Day 12 at a dose volume of 0.5 mL/kg (Table 1). The dosing schedule was designed to provide maximal anti-nicotine antibody levels during gestation. Groups 1 through 5 were comprised of 35 animals of which 25 does were subjected to Caesarean section and sacrifice on Gestation Day 29 for maternal and fetal evaluation and 10 does were allowed to deliver litters and assessed through Lactation Day 28. Groups 6 and 7 were comprised of 10 animals that were used for evaluation of nicotine levels in maternal and fetal blood at Gestation Days 20 and 29 (5 animals per group per day). A nicotine vaccine, NicVAX (AMNic-rEPA), was used for this study. NicVAX dose levels of 1.43 µg/kg and 35 µg/kg correspond to 1× and 25× the human dose on a weight/weight basis. The 35 µg/kg dose level corresponds to the full human dose of 100 µg when administered to a rabbit weighing 3 kg.

Groups 2, 5, 6 and 7 were implanted with osmotic pumps on Gestation Day 6 that continuously administered nicotine at a dose of 7 mg/kg/day. The pumps were removed on Gestation Day 20. This time period of nicotine administration was chosen to have the greatest potential effect on development of the fetus. The nicotine dose was selected to give a plasma nicotine level of 10-40 ng/mL, the level of a typical human smoker.

TABLE 1

Purpose and Number of Animals

| Group | Caesarian Section on Gestation Day 29 | Postnatal Phase through Lactation Day 28 | Nicotine and Cotinine Levels | NicVAX Dose Level □g/kg | Nicotine Dose Level mg/kg/day |
|---|---|---|---|---|---|
| 1 | 25 | 10 | — | 0 | NA |
| 2 | 25 | 10 | — | 0 | 7 |
| 3 | 25 | 10 | — | 1.43 | NA |
| 4 | 25 | 10 | — | 35 | NA |
| 5 | 25 | 10 | — | 35 | 7 |
| 6 | — | — | 10 | 0 | 7 |
| 7 | — | — | 10 | 35 | 7 |

Results indicated that there were no test article-related maternal deaths or clinical signs of toxicity during the study. NicVAX, administered on 3 occasions, at doses up to 35 µg/kg in New Zealand white rabbits, produced dose-dependent increases in anti-nicotine titers throughout the study.

In a similar study, there was a trend toward a higher percentage of live litters delivered in the vaccine group compared to the nicotine control group.

Example 2

100 female New Zealand White rabbits were tested according to the study design detailed below (Table 2). The vehicle/adjuvant and test article were administered via intramuscular injection. Nicotine was administered by osmotic pump infusion. The pumps were surgically implanted subcutaneously. The dose volume of the test article and vehicle was 0.5 ml/kg. The dose rate of the pumps was approximately 5 µl/hr.

Study Design

TABLE 2

| Group # | Dose level (µg/kg) | Test Article | # Females | Mortality |
|---|---|---|---|---|
| 1 | 0 | Vehicle/Adjuvant (IM) | 20 | 1 |
| 2 | 0 | Vehicle/Adjuvant (IM)/Nicotine (SC) | 20 | 3 |
| 3 | 1.43 | NicVAX (IM) | 20 | 0 |
| 4 | 35 | NicVAX (IM) | 20 | 0 |
| 5 | 35 | NicVAX (IM)/Nicotine (SC) | 20 | 1 |

The test article and vehicle/adjuvant formulations were administered to the study animals once at 30 days prior to gestation, once at 9 days prior to gestation, and once on day 12 of gestation. Beginning at day 6 of gestation, does in Groups 2 and 5 received nicotine subcutaneously via osmotic pumps for two weeks.

Results indicated that gestation food consumption was significantly decreased in comparison to controls in the vehicle/adjuvant (IM)/nicotine (SC) group from gestation day 6 through 29. This decrease in food consumption correlates with a decrease in maternal body weight and was considered treatment related. Gestation food consumption was significantly increased in the 35 µg/kg NicVAX (IM)/nicotine (SC) group during gestation day 0-18 and over the entire gestation period in comparison to the vehicle/adjuvant (IM)/nicotine (SC) group. These differences suggest a protective effect from the NicVAX, thereby reducing the effect of nicotine.

Regarding litter data (Table 3), in the vehicle/adjuvant (IM) group, 17 females delivered litters, two animals were not pregnant, and 1 animal was euthanized on gestation day 30. In the vehicle/adjuvant (IM)/nicotine (SC) group, 11 females delivered litters, 2 animals were not pregnant, 2 animals died pregnant, 5 animals aborted, and 4 animals delivered all dead kits. See Table 3. The inability of several females in the vehicle/adjuvant (IM)/nicotine (SC) group to successfully retain pregnancies to term and deliver viable litters was considered related to nicotine treatment.

In the 1.43 µg/kg NicVAX (IM) group, 16 females delivered litters, 3 animals were not pregnant, and 1 animal delivered all dead kits. In the 35 µg/kg NicVAX (IM) group, 19 females delivered litters. The pregnancy outcomes in the NicVAX treated groups were considered comparable to that in the vehicle/adjuvant (IM) controls.

In the 35 µg/kg NicVAX (IM)/nicotine (SC) group, 16 females delivered litters, one animal was not pregnant and two animals aborted. The increase in females in this group successfully retaining preganancies to term in comparison to the poor reproductive performance for the vehicle/adjuvant (IM)/nicotine (SC) group suggests that NicVAX exerts a protective effect on nicotine toxicity.

TABLE 3

| | Number of Does | | | | | | |
|---|---|---|---|---|---|---|---|
| Dose Levels | No. Animals | Found dead/euthanized in extremis | Abortion | Not Pregnant | No. Delivered | No. whole litters dead | No. Survived Day 28 |
| 0 (Vehicle/Adjuvant (IM)) | 20 | 1 | 0 | 2 | 17 | 2 | 15 |
| 0 (Vehicle/Adjuvant (IM)/Nicotine (SC)) | 20 | 2 | 5 | 2 | 11 | 4 | 6 |
| 1.43:g/kg NicVAX ™ (IM) | 20 | 0 | 1 | 3 | 16 | 1 | 15 |
| 35:g/kg NicVAX ™ (IM) | 20 | 0 | 0 | 1 | 19 | 4 | 15 |
| 35:g/kg NicVAX ™ (IM)/Nicotine(SC) | 20 | 1 | 2 | 1 | 16 | 5 | 11 |

TABLE 4

| Dose Level | Number of Kits (Mean) | | |
|---|---|---|---|
| (ug/kg) | Born | Liveborn | Stillborn |
| 0 (Vehicle/Adjuvant (IM)) | 8.1 | 8.1 | 0.1 |
| 0 (Vehicle/Adjuvant (IM)/Nicotine (SC)) | 6.8 | 5.3 | 1.4 |
| 1.43: g/kg NicVAX ™ (IM) | 8.0 | 7.9 | 0.1 |
| 35: g/kg NicVAX ™ (IM) | 8.1 | 7.3 | 0.4 |
| 35: g/kg NicVAX ™ (IM)/Nicotine (SC) | 8.8 | 6.9 | 1.3 |

TABLE 5

| Dose Level | Number of Kits (Mean) | | | |
|---|---|---|---|---|
| (ug/kg) | LD 0-7 | LD 7-14 | LD 14-21 | LD 21-28 |
| 0 (Vehicle/Adjuvant (IM)) | 84.2 | 99.4 | 98.5 | 98.2 |
| 0 (Vehicle/Adjuvant (IM)/Nicotine (SC)) | 47.8 | 100.0 | 100.0 | 100.0 |
| 1.43: g/kg NicVAX ™ (IM) | 93.0 | 98.4 | 96.6 | 99.3 |
| 35: g/kg NicVAX ™ (IM) | 75.9 | 90.4 | 97.5 | 98.9 |
| 35: g/kg NicVAX ™ (IM)/ Nicotine (SC) | 70.4 | 90.8 | 98.7 | 100.0 |

The mean number of kits born per litter was reduced in the vehicle/adjuvant (IM)/nicotine (SC) group in comparison to the vehicle/adjuvant (IM) group(Table 4). Likewise, the mean number of liveborn kits was significantly reduced along with significantly increased mean stillborn kits in the vehicle/adjuvant (IM)/nicotine (SC) group in comparison to the vehicle/adjuvant (IM) group. These differences are considered attributable to treatment with nicotine.

The mean number of kits born, live born and stillborn in the 1.43 µg/kg NicVAX (IM) and 35 µg/kg NicVAX (IM) groups were comparable to the vehicle/adjuvant (IM) group and unaffected by NicVAX treatment. The mean number of kits born in the 35 µg/kg NicVAX (IM)/nicotine (SC) group was statistically increased(8.8 kits/liter)in comparison to the vehicle/adjuvant (IM)/nicotine (SC) group with 6.8 kits/liter but was similar to the 35 µg/kg NicVAX (IM) group (8.1 kits/liter). This suggests that NicVAX is exerting a protective effect. See the tables above The mean lactation index, representing kit survival from lactation day 0-7 was 47.8% in the vehicle/adjuvant (IM)/nicotine (SC) group compared to the 84.2% in the vehicle/adjuvant (IM) control (Table 5). In the 35 µg/kg NicVAX (IM)/nicotine (SC) group, the mean lactation index was 70.4%, which again suggests that NicVAX exerts a protective effect on nicotine toxicity.

The invention claimed is:

1. A method for reducing at least one adverse effect of nicotine on a fetus, comprising administering a nicotine-carrier conjugate to a human pregnant with a fetus, wherein the carrier is an immunogenic protein, and wherein the adverse effect is selected from low birth weight, premature delivery/birth, post-natal nicotine withdrawal and fetal death.

2. The method of claim 1, wherein the fetus is exposed to nicotine via nicotine-containing smoke inhaled by the human pregnant with the fetus, a smokeless tobacco product or nicotine replacement therapy.

3. The method of claim 2 wherein the smoke inhaled by the human pregnant with the fetus is from a cigarette, pipe or cigar.

4. The method of claim 2, wherein the smokeless tobacco product is selected from the group consisting of a nicotine transdermal patch, chewing tobacco, snuff, tobacco pouches, nicotine-containing chewing gum, inhaler, nasal spray, tobacco lozenges, and sucker.

5. The method of claim 3, wherein the smoke is second-hand smoke.

6. The method of claim 1, wherein the human smokes at least about 1 cigarette per day.

7. The method of claim 1, wherein the human has a plasma nicotine level of a chronic smoker.

8. The method of claim 1, wherein the nicotine-carrier conjugate is administered in a dose of about 0.35 µg/kg to about 6 µg/kg.

9. The method of claim 1, wherein the human has a plasma nicotine level of an occasional smoker.

10. The method of claim 1, wherein the human has a plasma nicotine level that is detectable.

11. The method of claim 10, wherein the human has a plasma nicotine level of at least about 10 ng/mL.

12. The method of claim 1, wherein one dose of nicotine carrier conjugate is administered to the human.

13. The method of claim 1, wherein multiple doses of nicotine carrier conjugate are administered to the human.

14. The method of claim 12 or 13, further comprising administering the nicotine carrier conjugate to the human before she becomes pregnant.

15. The method of claim 12 or 13, wherein the nicotine carrier conjugate is administered to the human after she becomes pregnant.

16. A method for increasing the gestation time of a fetus to the maximum normal gestational period in a pregnant human exposed to nicotine, comprising administering a nicotine-carrier conjugate to the pregnant human, wherein the carrier is an immunogenic protein.

17. A method for reducing the risk of spontaneous abortion of a fetus from a pregnant human exposed to nicotine, relative to the risk of abortion in a pregnant human not exposed to nicotine, comprising administering a nicotine-carrier conjugate to the pregnant human, wherein the carrier is an immunogenic protein.

18. A method for increasing the fertility of a female human exposed to nicotine, comprising administering a nicotine-carrier conjugate to the female human, wherein the female human is attempting to get pregnant, wherein the carrier is an immunogenic protein.

19. A method for inducing a protective response against nicotine in a human pregnant with a fetus, comprising administering a nicotine-carrier conjugate to the pregnant human at least one time during pregnancy, wherein the carrier is an immunogenic protein.

20. The method of claim 12, wherein the nicotine-carrier conjugate is administered in a dose of about 0.35 µg/kg to about 6 µg/kg.

* * * * *